United States Patent [19]

Lawson et al.

[11] Patent Number: 5,319,578

[45] Date of Patent: Jun. 7, 1994

[54] YARN PROFILE ANALYZER AND METHOD

[75] Inventors: John B. Lawson, Providence; Kendall W. Gordon, Jr., North Kingstown, both of R.I.

[73] Assignee: Lawson-Hemphill, Inc., Central Falls, R.I.

[21] Appl. No.: 950,830

[22] Filed: Sep. 24, 1992

[51] Int. Cl.$^5$ .............................................. G01B 11/08
[52] U.S. Cl. ..................................... 364/563; 250/560
[58] Field of Search ............... 250/560, 561, 562, 548; 364/563

[56] References Cited

U.S. PATENT DOCUMENTS

| | | | |
|---|---|---|---|
| 4,152,767 | 5/1979 | Laliotis | 250/560 |
| 4,465,937 | 8/1984 | Forbes | 250/560 |
| 4,585,947 | 4/1986 | Liptay-Wagner et al. | 250/560 |
| 4,753,532 | 6/1988 | Aldred | 250/560 |
| 4,885,709 | 12/1989 | Edgar et al. | 364/563 |
| 4,887,155 | 12/1989 | Massen | 250/560 |
| 5,088,827 | 2/1992 | Kyriakis | 250/561 |

FOREIGN PATENT DOCUMENTS 2236387  4/1991  United Kingdom ................ 250/360

Primary Examiner—Jack B. Harvey
Assistant Examiner—Thomas Peeso
Attorney, Agent, or Firm—Brian M. Dingman

[57] ABSTRACT

A yarn profile analyzer and method in which the yarn is moved under substantially constant tension through an imaging area including a light source and a spaced light sensing array. The width of closely spaced portions of the yarn passing through the imaging area is then determined from the array output, and the widths are stored and then analyzed for a variety of parameters.

30 Claims, 9 Drawing Sheets

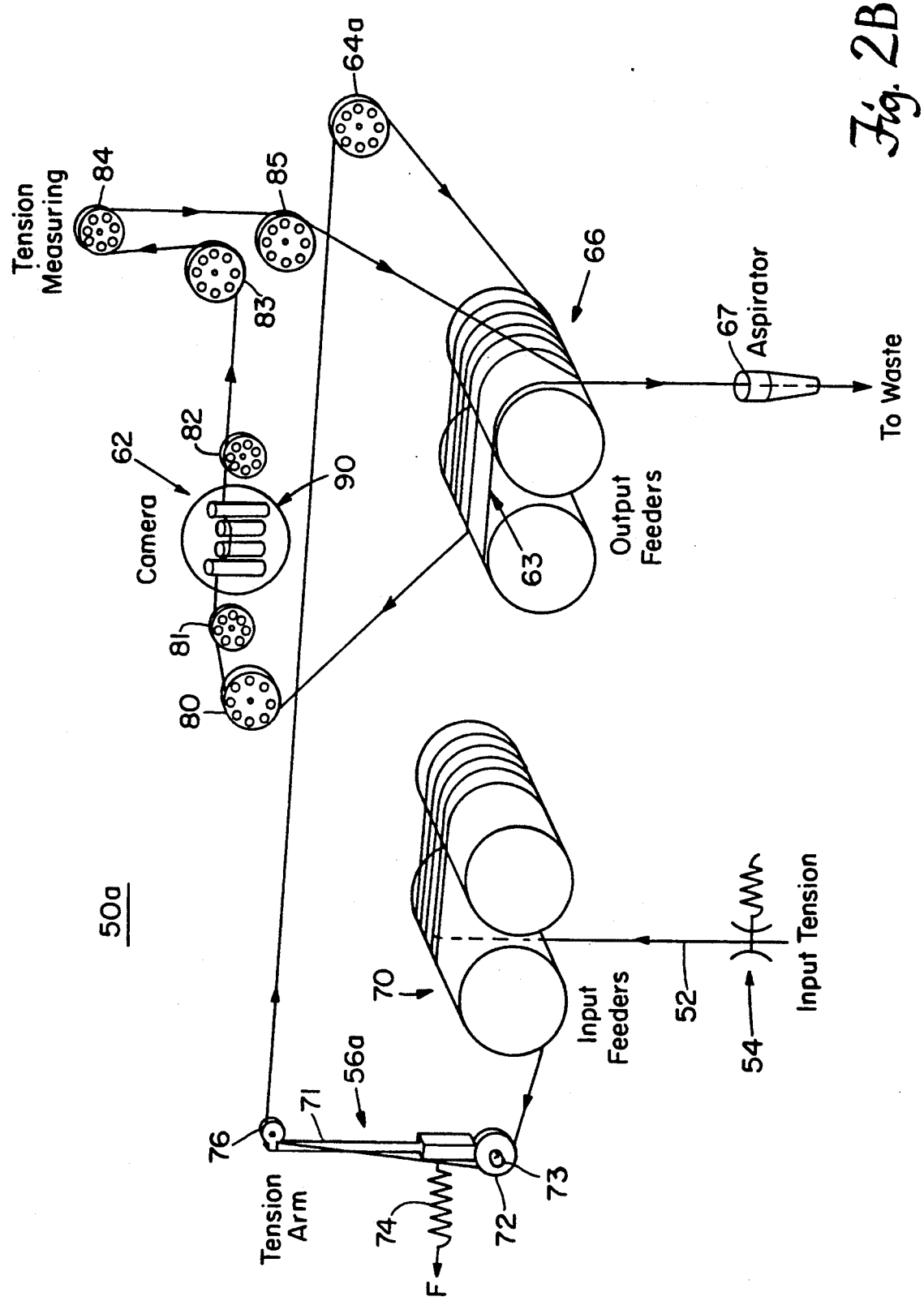

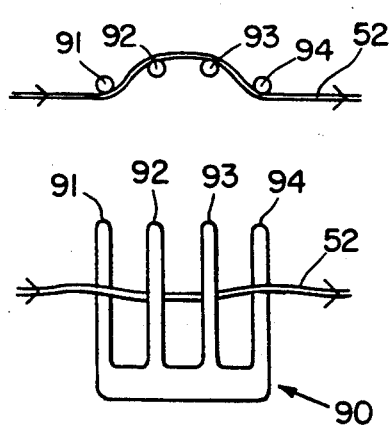
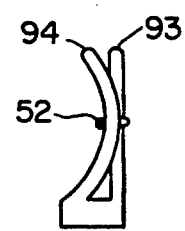
Fig. 3C
Fig. 3A
Fig. 3B
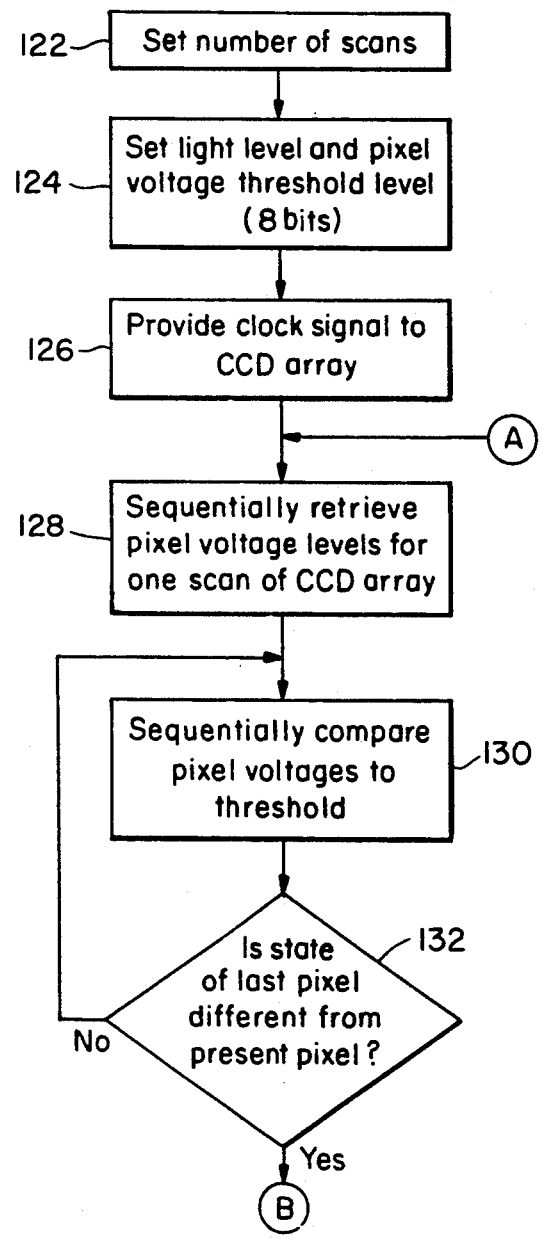
Fig. 4A

YARN PROFILE ANALYZER AND METHOD

FIELD OF INVENTION

This invention relates to a yarn profile analyzer and method in which enlarged images of a moving yarn held at constant tension are taken at closely spaced intervals with a CCD camera to capture and allow the analysis of a profile of a length of yarn.

BACKGROUND OF INVENTION

It is desirable to know as much as possible about yarn before it is used to manufacture fabric or other products. If the yarn does not have the desired properties, there can be problems in the finished product. Accordingly, it is the desire of the industry to obtain as much information as possible about as much as possible of the yarn being used to make the product. This has created a great demand for automated equipment for analyzing yarn.

In the past there have been developed devices using digital cameras such as CCD arrays to scan moving yarn, and store the scans in a computer, or print them out for analysis. One such device is disclosed in U.S. Pat. No. 4,764,876. That device is adapted for measuring balloons and entanglements in textured yarn by looking for transitions from thin to thick yarn and vice versa. Although such information is useful, the device does not have the versatility to provide more information about the yarn for a variety of reasons, including the fact that the width of the yarn is determined to be the number of pixels that are blocked from receiving light in a given scan of the CCD array. Thus, the device is not sensitive to loops in textured yarn or hairs in cotton yarn. In addition, the tension applied to the yarn under test is unknown. Accordingly, the yarn measurements from cone to cone are dependent on the external yarn-moving machinery of the yarn producing device, and thus subject to inconsistencies. Also, the yarn is not carefully guided or flattened while it is being imaged, leading to additional measurement inconsistency and error.

SUMMARY OF INVENTION

It is therefore an object of this invention to provide a yarn profile analyzer and method which provides accurate, reproducible data.

It is a further object of this invention to provide such a device and method which is not dependent on external equipment for its accuracy.

It is a further object of this invention to provide such a device and method which produces data not heretofore available in automated yarn measurement systems.

It is a further object of this invention to provide such a device and method that can be used to test for integrity of textured or entangled yarn.

It is a further object of this invention to provide such a device and method that can identify various types of faults in a single yarn test. For example: tight spots, untextured spots and long loops in air textured yarn, and hairiness and core evenness in cotton or spun yarns.

This invention results from the realization that the accurate, reproducible measurement of the profile of a moving yarn may be accomplished by applying a substantially constant tension to the yarn as it moves through an imaging area and capturing the imaged widths of the yarn at high speed for analysis of the profile for a variety of parameters.

This invention may be accomplished in the yarn profile analyzer and method. The yarn to be imaged is moved under substantially constant tension through an imaging area including a light source and a spaced light sensing array having an output. Then, from the output of the measuring array, the widths of closely spaced portions of the yarn passed through the imaging area are determined. Preferably, the yarn is spread as it passes through the imaging area, for example by pulling the yarn over a hard surface before it enters the imaging area. The substantially constant tension is preferably adjustable so that the operator can establish the amount of tension applied to the yarn in the measuring area. The substantially constant tension may be provided with a biased pivoting arm over which the yarn travels, with the bias level adjustable.

The yarn speed as it moves through the imaging area may be made adjustable so that it can be controlled by the operator. The yarn may be moved by a pair of driven rollers downstream of the imaging area. The light sensing array may include a plurality of linearly-arranged light-sensing elements. In that case, the determined width of the yarn may be based on the furthest-spaced pair of elements blocked from receiving light by the yarn. The level of received light compared to the maximum light level at which elements of the sensing array are considered blocked is preferably adjustable so that the operator may adjust the sensitivity of the measurements.

The yarn image is preferably magnified by a magnifying lens arrangement in front of the sensing array for increasing the array resolution. The light source is preferably designed to have an adjustable output to provide fine control over the image of the yarn.

The measured widths are preferably stored for further processing. The processing may include means for establishing a yarn width threshold and then counting the number of yarn widths greater than or less than the threshold. Additionally, there may be means for establishing a width zone above and below the threshold. There may also be means for establishing a minimum number of consecutive determined widths that must be greater than or less than the threshold in order to register a yarn event. Additionally, there may be means for resolving from the determined widths when a local maximum or minimum width has been reached. There may also be means for skipping a desired yarn length after registration of an event.

DISCLOSURE OF PREFERRED EMBODIMENTS

Other objects, features, and advantages will occur to those skilled in the art from the following description of a preferred embodiment and the accompanying drawings in which:

FIG. 2B is a more detailed schematic view of the analyzer of FIG. 2A;

FIGS. 3A through 3C are front, side and top views, respectively, of the yarn centering and flattening device of the analyzer of this invention; and FIGS. 4(a) and 4(b) is a flowchart of a preferred form of yarn diameter measurement accomplished by the system and method of this invention;

Figure 8A:
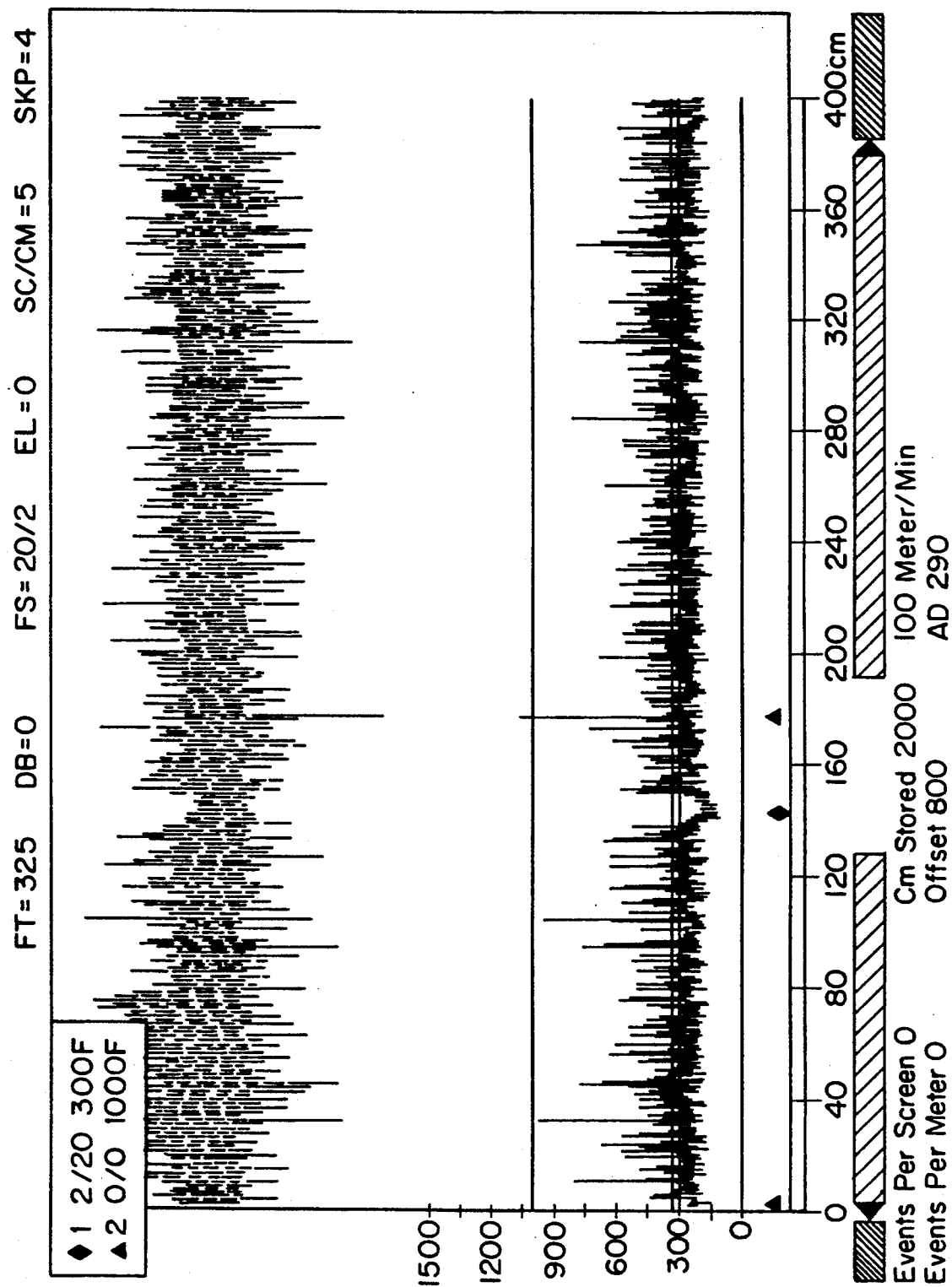
Figure 8B:
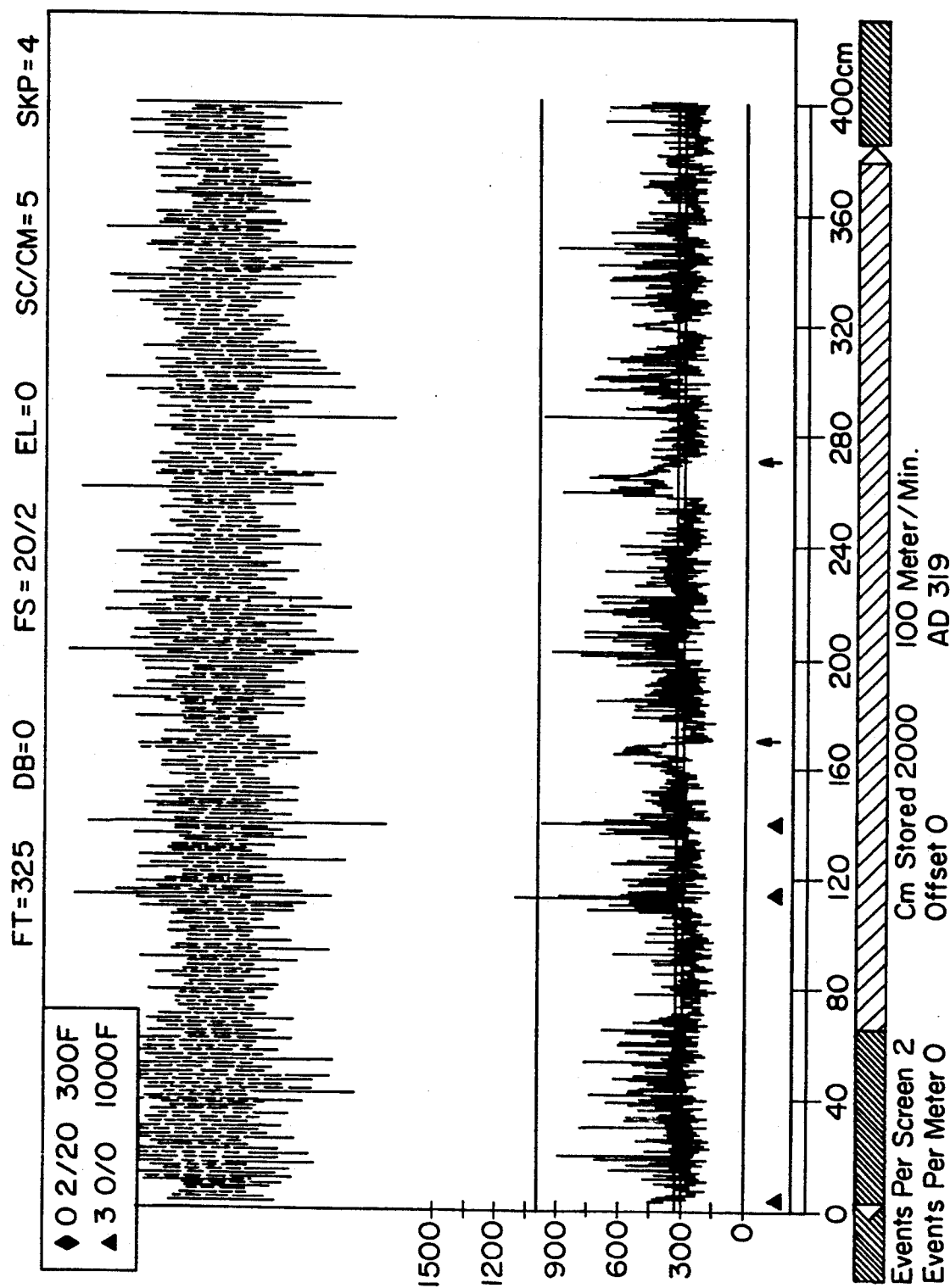
Figure 9:
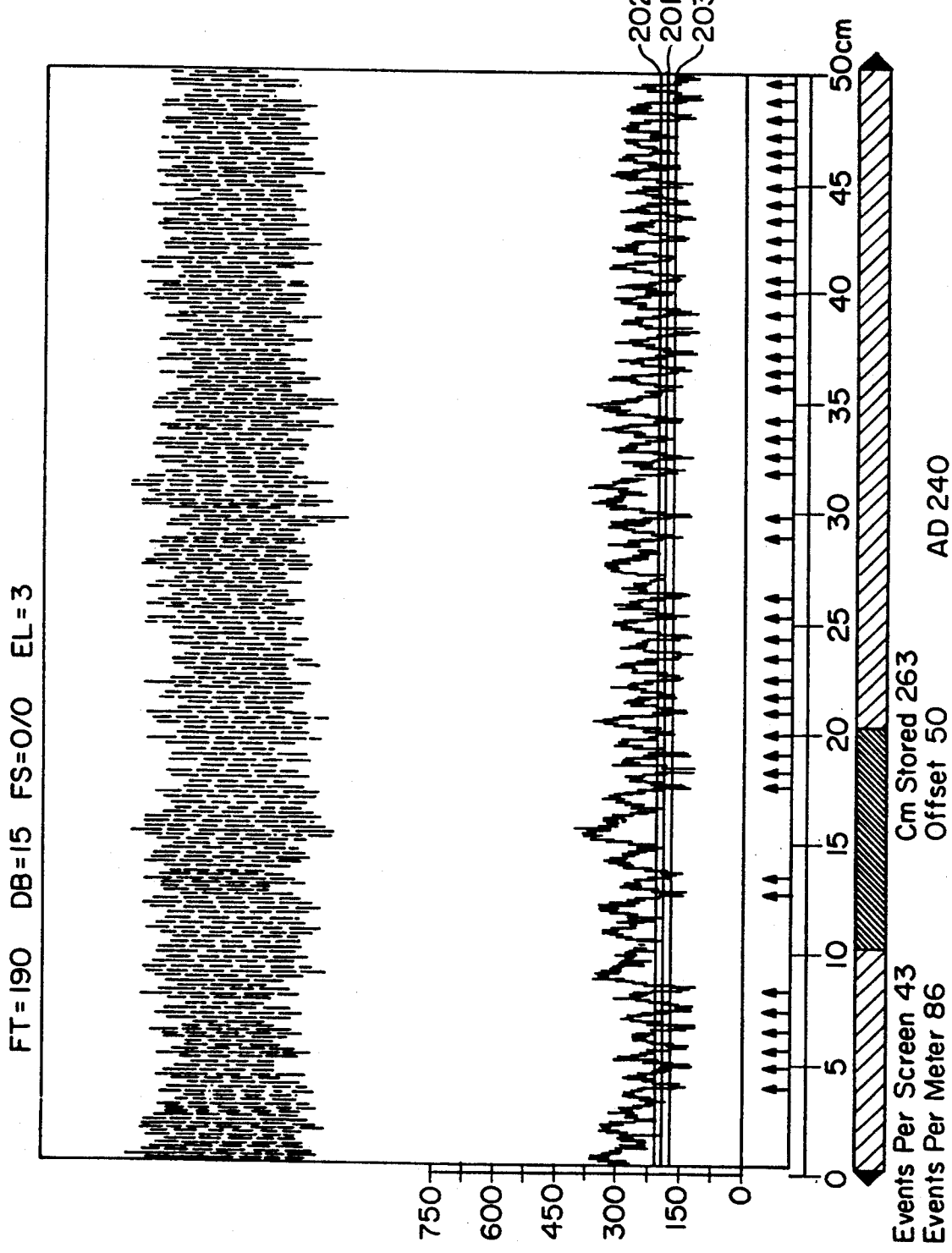

FIGS. 8(a) and 8(b) is an example of a printed output of the system and method of this invention showing a triple-threshold measurement of an air textured yarn; and FIG. 9 is a similar output showing the use of the dead band and length filters of the system and method of this invention in a measurement of an entangled yarn.

Figure 1:
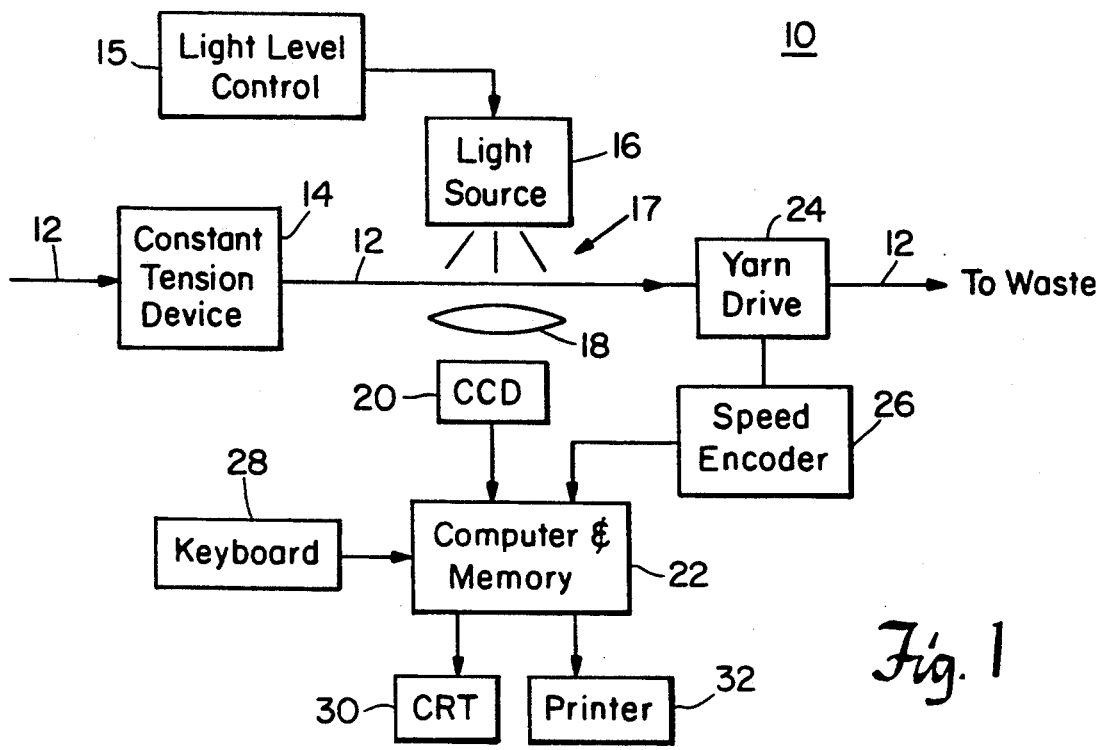
FIG. 1 is a schematic diagram of a yarn profile analyzer according to this invention which may also be used to practice the method of this invention.

There is shown in FIG. 1 yarn profile analyzer 10 according to this invention which may also be used to practice the method of this invention. Analyzer 10 is used to make width or profile measurements of yarn 12 moved through imaging area 17 by yarn drive 24. Yarn 12 passes through constant tension device 14 before entering area 17 so that it is under a constant, reproducible tension while being imaged. This provides the ability of device 10 to develop useful, accurate, quantitative data concerning each cone of yarn that is measured with the device, independent of any external equipment such as the machinery used to produce the yarn or any other production equipment. Light source 16 provides sufficient light in imaging area 17 so that the image focussed by lens 18 onto CCD array 20 is sharp enough for the desired purposes. Light level control 15 allows operator control of the light output level of light source 16. Preferably, light source 16 is an incandescent lamp, and control 15 is a regulated DC lamp power supply with variable output to provide a variable, steady light source without 60 Hz flicker. CCD 20 is preferably a linear CCD array having 2,048 pixels spaced on 13 micron centers. Lens 18 preferably magnifies the image four times so that a quarter-inch wide yarn fills the entire one inch array. The amount of light sensed by each pixel of array 20 is provided as a related voltage at the output of array 20. This level can be compared to an adjustable, operator established threshold level in computer 22 so that the device reports a blocked unlighted pixel when only the selected percent of the maximum possible incident light is received. For example, the device could be enabled to report blocked pixels when the received light is 20% less than the maximum light incident on the device with no yarn present in the measurement area.

The light intensity of the lamp and therefore the level of the maximum CCD array voltage output is adjusted by regulating the voltage of the light power supply. The light is preferably provided to measurement area 17 using a randomly-oriented-fiber fiber optic bundle that carries light from the lamp. The fiber orientation tends to average lamp output levels to provide a more even light source for more accurate and repeatable measurements. The light level and threshold level are measured on a scale of 256 units. The light level is set by first setting the adjustable threshold to a desired light level and then adjusting the voltage of the light power supply until the received light level matches the selected threshold level. Then, the threshold can be reset to a desired percent level below the incident light level to establish the level at which pixels are considered blocked. The system can then be tested with a straight clean test wire with a known diameter to evaluate the operation of the light source and the CCD array; the measured diameters should closely match.

In one example, where the threshold is set at 80% of the received light level, the diameter of a measured section of yarn was 281 pixels. When the threshold was lowered to 60% of the light level, the diameter of the same section of yarn was measured as 138 pixels. This variation is due to the fact that yarns have a variety of translucencies and fine filaments or hairs that only partially block individual pixels. Thus, a high threshold level increases the sensitivity of partially-blocked pixels and thus the number of hairs that are counted, and in effect enlarges the measured core of the yarn, whereas a low threshold level filters out the hairs to show variations in the core or body of the yarn only, such as the thick and thin spots of a spun yarn. Thus, the device of this invention allows the selected measurement of the core or more than the core of the yarn as desired.

Encoder 26 is preferably used to measure the lengths of yarn transported by drive mechanism 24, which is then translated into yarn lengths and then yarn speed by computer 22. Keyboard 28 is used by the operator to enter commands for operation of computer 22 in a known fashion. The output of the device may then be applied to either CRT 30 or printer 32 as desired and explained more fully below.

Figure 2A:
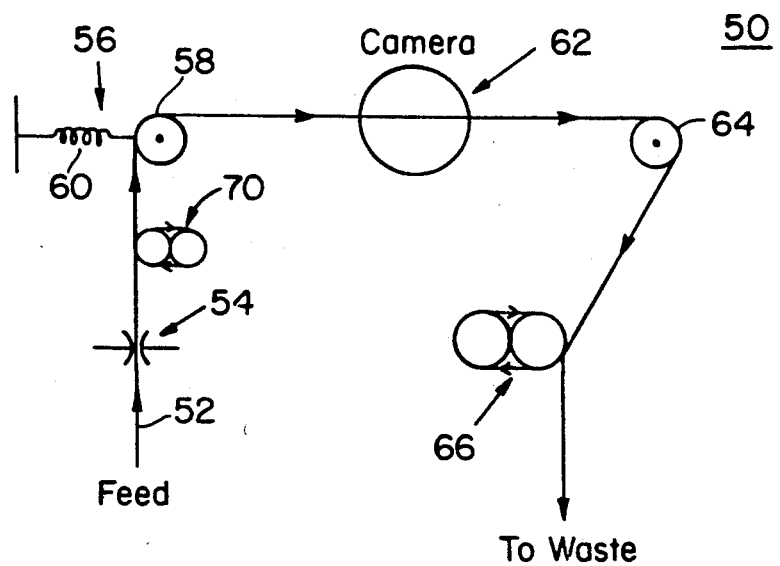
FIG. 2A is a highly schematic view of a preferred embodiment of the analyzer of FIG. 1.

Embodiment 50 of this invention is shown very schematically in FIG. 2A. Yarn 52 preferably fed off the cone of yarn is sent through pretension device 54, around a first set of driven feed rolls 70, and then through constant tension device 56 schematically depicted as roller 58 and adjustable tension spring 60. Device 56 preferably allows the operator to select the tension applied to yarn 52 from ½ to 750 grams. Camera 62 images the yarn and provides the image to the computer. In a preferred embodiment, the linear CCD array described above is employed and operated at about 3,200 scans per second with 10,000 yarn diameters measured and stored in one meter of yarn with the yarn running at 20 meters per minute. This is accomplished with a clock running at approximately 15 megahertz. The yarn is then directed by roller 64 to driven roll pair 66 around which yarn 52 is wound one or more times to pull the yarn in front of camera 62.

A preferred embodiment showing one application of system 50a is shown in more detail in FIG. 2B. Input tension device 54 may be a standard compensating tension device to provide a small tension against which input feed roll pair 70 pulls. The yarn is wrapped around roll pair 70 a number of times and then travels over constant tension device 71 that may be the type of adjustable constant tension arm shown in U.S. Pat. No. 3,575,360, which consists of tension arm 56a pivoting on point 73, to which is applied a force in the direction of arrow F by adjustable tension spring 74. Top roller 76 applies the tension to the yarn and directs it either directly to the imaging area, or to roller 64a. The yarn path in FIG. 2B is different than that in FIG. 2A to illustrate an alternative in which the reaction of the yarn to various tensions can be measured. This setup allows the application of a desired first tension to the yarn by tension arm 56a to allow the testing of the integrity or fastness of textured yarn, and of entanglements in entangled yarn. Entanglement integrity is important data because the entangled yarn will be subjected to tension in the production equipment in which the yarn is used.

Thus, if a relatively low tension pulls out the entanglements, the yarn may not be suitable for use in the production equipment. In this case, a relatively high tension can be applied by tension arm 56a, and no measurements are taken on the yarn in this state; the high tension is just used as a means of testing the integrity of the entanglements because the entanglements in poorly entangled yarn will at least partially pull out under the relatively high tension of say 500 grams. After passing over roller 64a the yarn is then wrapped a number of times around output feeder roll pair 66 and then provided up to rollers 80 through 85 under a low tension as controlled by the number of wraps 63 around output roll pair 66 downstream of roller 85. Varying the number of wraps varies the yarn slippage on the rollers of pair 66. The yarn is then moved to waste by air aspirator 67. The tension in measurement area 62 is measured at rollers 83 through 85 as is known in the art so that the test conditions are known. Yarn guide 90 is used in the yarn measurement area to make sure the yarn is centered within the measurement area and also to flatten out the yarn to make better measurements on the yarn.

Device 90 is shown in more detail in FIGS. 3A through 3C. The device includes two "C" shaped fingers 91 and 94 offset from straight center fingers 92 and 93 to create a "C" shaped path for the yarn to traverse so that the yarn is pulled over the edges of the fingers to flatten and spread the yarn slightly so that it presents a better, flatter profile in the measurement zone, preferably between fingers 92 and 93. Other guides include V-groove device, or a pin over which the yarn may be pulled.

In conjunction with the variable light level and variable CCD pixel threshold of this invention, the device is enabled to detect loops and hairs to a desired level so that relatively gross or relatively fine measurements can be made of the yarn profile or diameter. Also contributing to this measurement sensitivity is the use of the system in a manner in which the measured diameter of the yarn is taken as the greatest distance between blocked sensing array pixels. Accordingly, a hair or loop in the yarn passing in front of the array will cause the measurement of a larger yarn profile (diameter), even if there is a gap between the main body of the yarn and the loop. Thus, the device truly measures the total yarn width at the point of measurement.

Figure 4B:
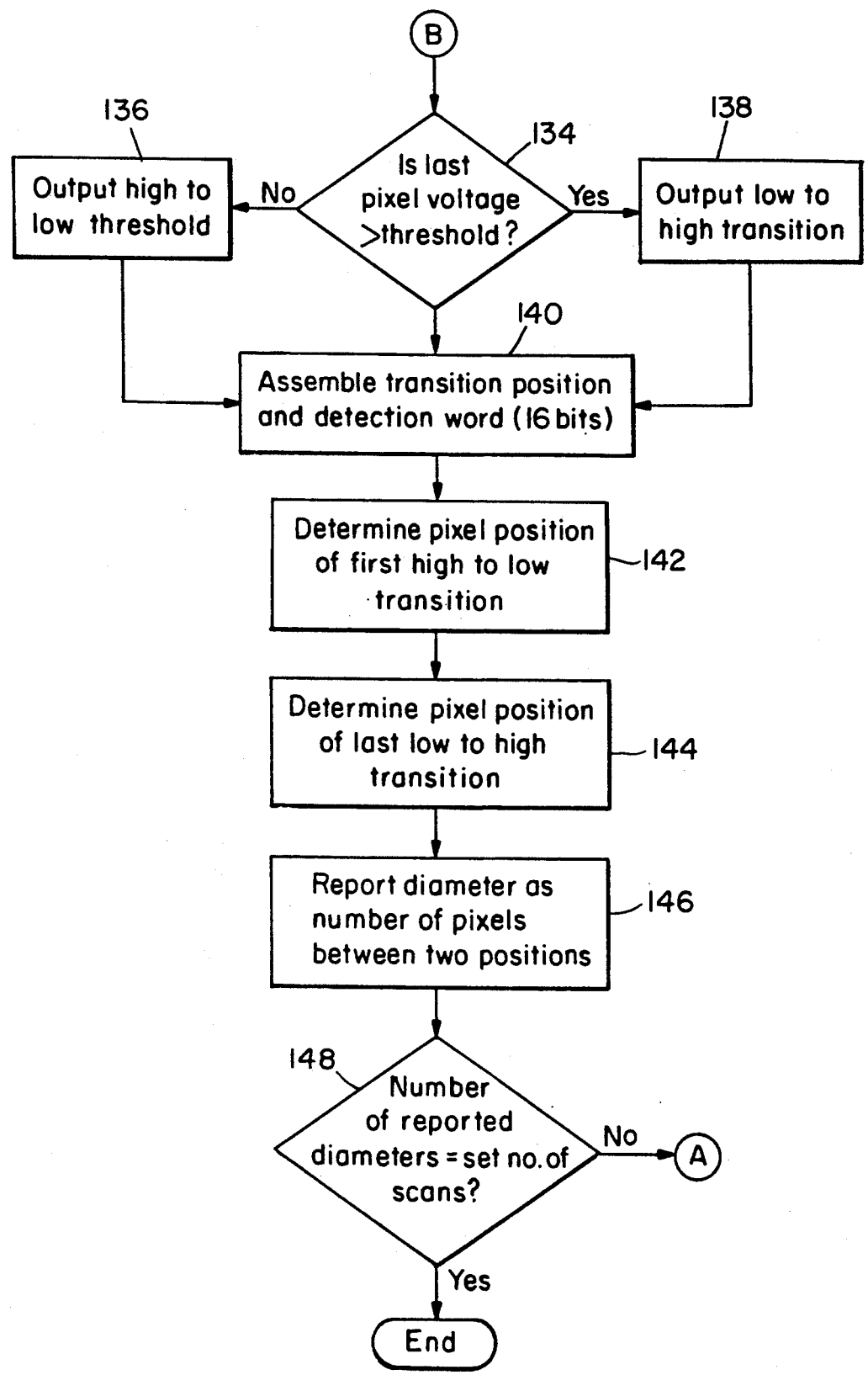

FIGS. 4((a) and (b)) details flow chart 120 for the system and method of this invention in which a large number of measurements of the yarn moving through the imaging area are taken and sent to the memory of computer 22, FIG. 1. First, the operator establishes a number of scans (yarn width measurements) to be taken in the test, step 122. The operator then sets the output level of the incandescent lamp used as a light source, and the pixel voltage threshold level, step 124. Preferably, the analog output from the CCD array can be displayed as 256 light levels. The pixel voltage threshold level is then chosen as a value between 0 and 255 which is less than the array output when there is nothing blocking the light received by the array. For example, the unblocked light level may be set at 200 units, and the pixel voltage threshold level may be set at 80% of 200, or 160 units. Then, if the light received by a pixel of the CCD array is less than 80% of the maximum (a reading of less than 160 units), the system interprets that the pixel is blocked from receiving light, translated into a low level digitized signal. A high level indicates an unblocked pixel.

The computer provides a clocking signal to the CCD array, step 126. Then, each clock pulse controls the output of the analog voltage of one element of the array. In step 128, the system sequentially receives the pixel voltage levels for one scan of the pixels of the linear CCD array. These values are then sequentially compared to the pixel voltage threshold level to determine whether the pixels are to be considered open or blocked, step 130. At step 132, the system determines if the state (open or blocked) of the last (current) pixel is different from that of the previous pixel. If so, there has been a transition from unblocked to blocked, or blocked to unblocked, and at step 134 the system determines if that last pixel voltage is greater than the threshold. If it is, that means that this last pixel is unblocked and since there has been a change, the previous pixel was blocked. Therefore, the system reports a low to high transition, step 138, and provides a 16 bit word which represents the position and direction (low to high or high to low) of that transition. Each transition results in one 16 bit word. If the last pixel voltage is not greater than the threshold, the system outputs a high to low threshold, step 136.

The words assembled in step 140 thus establish the location and direction of each transition caused by the yarn blocking light received by the CCD array. The system at step 142 then determines the pixel position of the first high to low transition, and in step 144 the position of the last low to high transition. At step 146 the system then reports the diameter of the measured yarn as the number of pixels between the two determined positions. Accordingly, the system is enabled to measure the yarn diameter as the distance between the first blocked pixel and the last blocked pixel regardless of the state of the intervening pixels. Thus, if a yarn is hairy or has loops, and the light level and pixel threshold level are set so that those hairs or loops are detected at least to some extent, the width reported will be the distance between the uppermost and lowermost loops or hairs. By adjusting the pixel voltage threshold downward, the smaller hairs or loops, or less dense areas of hairs or loops, can be ignored to provide a system with a flexibility to measure desired yarn parameters. For example, the threshold can be set very low so that the dense core of the yarn is measured. Alternatively, the system can be made extremely sensitive to the hairs or loops so that the measurement is close to the total effective diameter of the yarn. At step 148, the system compares the number of scans or diameters it has reported to the number of scans chosen by the operator so that the test ends after the chosen number of diameters have been measured. Preferably, the system is enabled to allow the operator to choose to not report certain scans, effectively skipping scans between scans that are reported. This allows the operator to choose an overall length of yarn to be tested and the distance between measured diameters with a system having a fixed clock frequency. This is accomplished by the operator setting the yarn velocity and choosing which measurements are to be reported.

As described in more detail below, the system allows the operator to establish a fixed or variable threshold yarn diameter level to which the measured diameters are compared. Preferably, the output is reported in pixels. Thus, in the outputs as shown in FIGS. 8 and 9, for example, there may be plotted at the lower portion of the figures the measured yarn diameters in pixels on the Y axis, and the length on the X axis. The second output across the top is a representation of the actual profile of the yarn, showing more graphically the hairs, thin spots, and thick spots, for example.

The system allows the operator then to establish one or more threshold values against which the measured diameters are compared to report an event. For example, the system could be enabled to report an event whenever the measured diameter exceeds 600 pixels. Alternatively, an event could be defined as each crossing of that 600 pixels threshold in either direction. For measuring entangled yarn, an event is preferably determined to be each downward-moving crossing of the threshold that is preceded by a maximum reading. Accordingly, the events in this case would indicate the presence of an entanglement preceded by a balloon.

Figure 5:
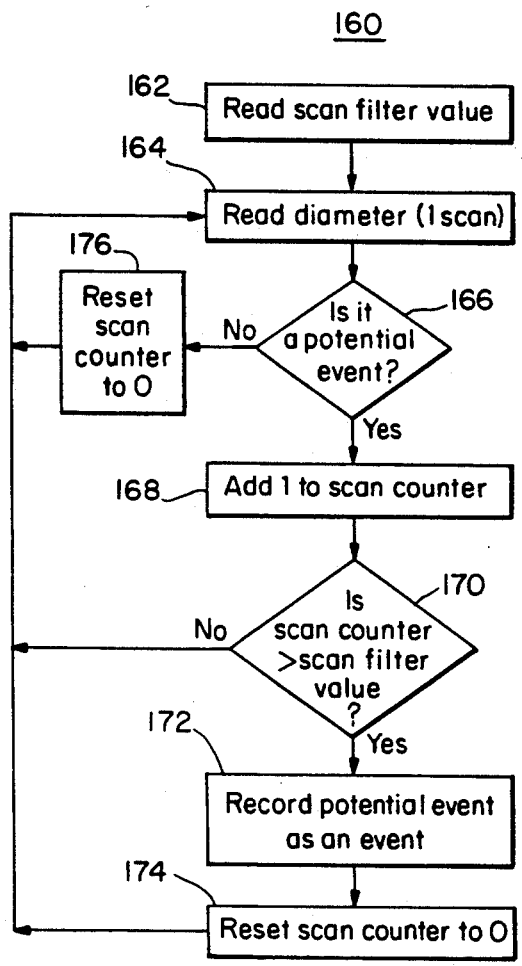
FIG. 5 is a flow chart of the scan filter of the system and method of this invention.
Figure 6:
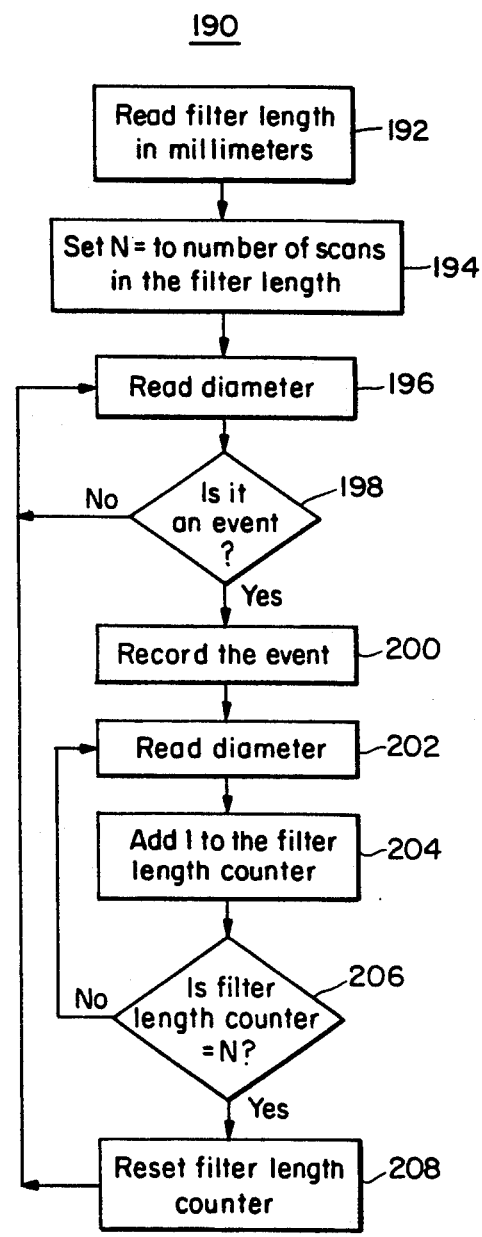
FIG. 6 is a flow chart of the length filter of the system and method of this invention.

The thresholds and filters of this invention allow the system, which reports yarn diameter in number of pixels, to be used to test for desired parameters of the yarn. The scan filter depicted by flow chart 160, FIG. 5, only reports an event when there are a chosen number of consecutive yarn width readings above and/or below the desired level. This effectively filters out extraneous events or small variations in yarn diameter to report only true events. In step 162, the system reads the scan filter value set by the operator. Typical scan filters might be 20 scans above the line and 2 scans below the line for an air textured yarn. The system in step 164 then reads a diameter and determines whether or not it is a potential event in step 166. For example, if an event is a local maximum diameter, there would be a potential event if the read diameter is greater than the last diameter.

For entangled yarn, to register an event there must be a measurement of yarn diameter below the threshold, followed by a measurement above the threshold, and then a movement back down below the threshold. In that example, the scan filter then only arms the system to look for an event when there have been a chosen number of consecutive yarn diameters greater than the threshold (a balloon). Then, the system employs the below the threshold scan filter to look for a thin spot following that maximum. For example, if the scan filter is 2 above and 2 below the line for an entangled yarn, an entanglement will be found only when there is a balloon taking up at least two consecutive above-the-threshold width measurements, followed by an entanglement taking up two consecutive below-the-threshold width measurements.

An event is a targeted characteristic of the yarn, defined by selected thresholds and filters, that is to be counted. If there is a potential event, the number 1 is added to the scan counter, step 168, and if the scan counter is greater than the scan filter value, step 170, the potential event is recorded as an event, step 172, and the scan counter is reset to 0, step 174. If the scan was not a potential event, the scan counter is reset to 0, step 176, and operation returns to step 164.

A second filter accomplished by this invention is called a length filter. This filter allows the operator to choose a distance following an event in which the measured diameters will not be used to look for another event. Typically, this filter may be used to filter out small unexpected changes in yarn diameter that the operator does not desire to see. For example, when the operator desires to measure entanglements in an entangled yarn, the operator may desire to filter out small unexpected threshold crossings that are too early for a valid new entanglement count. Then, the operator can set the length filter to ignore crossings of the threshold that occur earlier than the event length he is looking for, so that the system reports only the true entanglement events. In step 192 the system reads the filter length in millimeters. Preferably, the operator selects the filter length based on a small percent of the anticipated event length, and the system interprets this in millimeters based on the scan frequency and yarn speed. The system then sets the number of scans to be skipped that make up that filter length, step 194, and reads the diameter, step 196. If the diameter is an event, step 198, the event is recorded, step 200 and the next diameter is read, step 202. The number 1 is then added to the filter length counter, step 204, and if the filter length counter does not equal N, operation moves back to step 202 to continue reading diameters so that N diameters are skipped. When that number of diameters has been read following the event, the filter length counter is reset, step 208, and operation returns to step 196.

Figure 7:
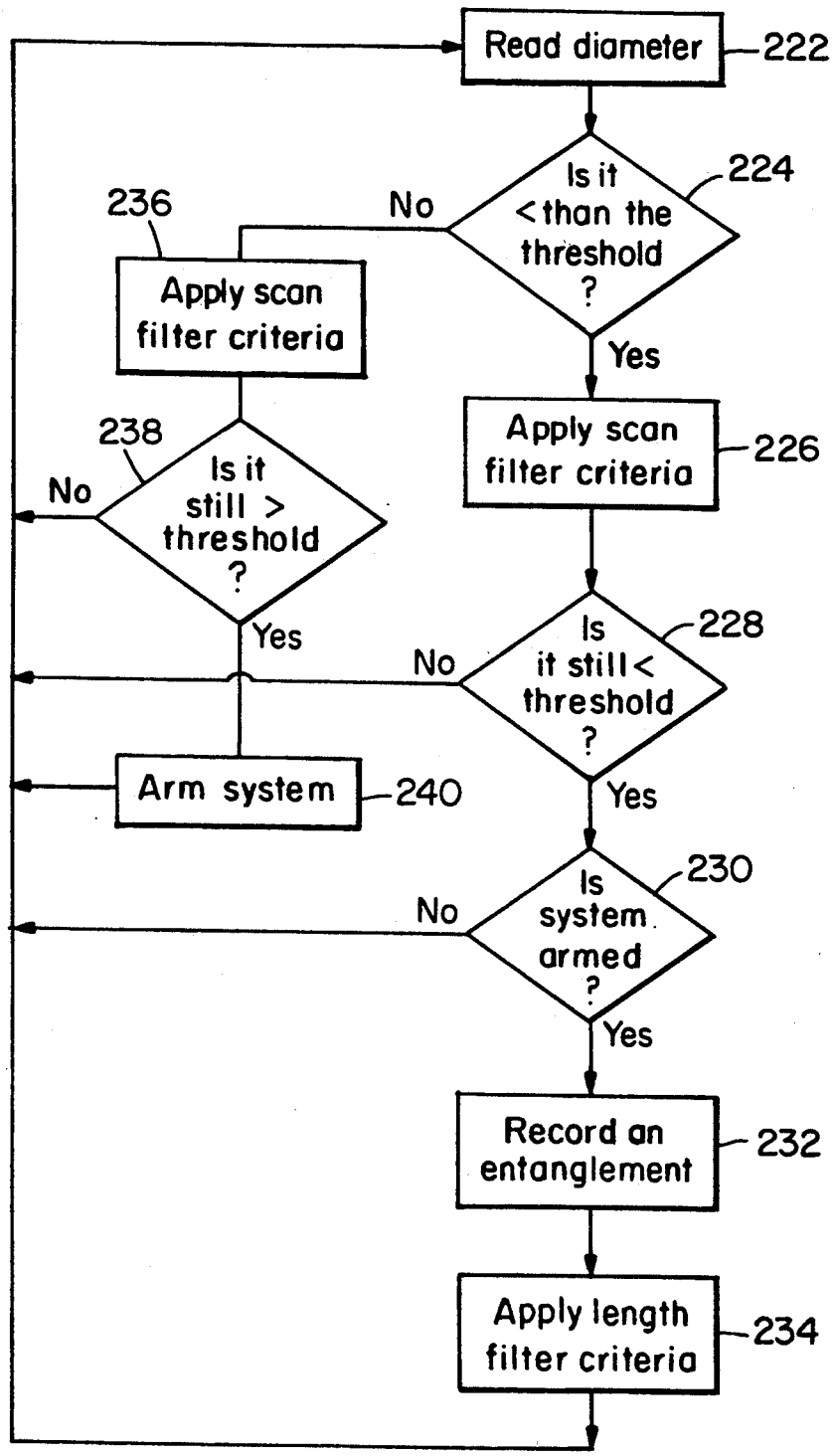
FIG. 7 is a flow chart of an example of the application of the scan filter and length filter detailed above to measurement of an entanglement in an entangled yarn.

FIG. 7 details flow chart 220 of the application of the scan filter and length filter of an entanglement by the system and method of this invention. In step 222, a diameter is read and if it is less than the threshold, step 224, the system applies a scan filter criteria, step 226. If the diameter is still less than the threshold, step 228, and the system is armed, step 230, the system records an entanglement and applies the length filter criteria, steps 232 and 234. Arming is the crossing of a targeted threshold and filter selection in the opposite direction from an event count. The system must arm between event counts. If the diameter is not less than the threshold the scan filter criteria are applied, step 236, and if the diameter is still greater than the threshold, step 238, then the system is armed to look for an event, step 240.

FIGS. 8((a) and (b)) and 9 are two outputs from the system and method of this invention showing the diameter measurements, thresholds, and filters. As described above, the lower graph line of FIG. 8 is an output of the measured diameters in pixels. In this case, the measurements vary from approximately 150 to approximately 1,050 pixels. What shown in total two pages of FIG. 8 is approximately 800 centimeters of the 2,000 centimeters stored in the system. In this case 10,000 yarn scans were stored over the 2,000 centimeters making five scan per centimeter of the yarn moving at 100 meters per minute. The top graph line of FIG. 8 is a representation of the profile of the yarn consisting of 4,000 widths. FIG. 8 details three fixed yarn diameter thresholds, at 300, 325, and 1,000 pixels. These are depicted by horizontal lines on the output. Each of the fixed thresholds has applied to it a scan filter above and below the threshold as shown in the boxes at the upper left hand corners of the two pages of the figures, and across the top of the second page. An event meeting a criteria established by the threshold and the scan filters is recorded with a unique shaped icon at the lower portion of the graphical output at the location of the event. Thus, a diamond is used to show the location of an event at a 300 threshold with a two scan filter above the line and a 20 scan filter below the line. Accordingly, this finds a long thin or tight spot in a textured yarn of at least 20 scans following a short thick spot of at least two scans above the line. In this case, one such event was found at approximately 140–150 centimeters into the yarn. Looking vertically above the diamond one can see the tight spot indicated in the lower output by a continuous area below 300 pixels and looking above that one can see the representation of this area as a long entanglement or tight spot.

Of course, since the light level and the pixel threshold value are chosen as desired, these measurements are not absolute. However, because the light level and pixel threshold values are determined with great accuracy, the system and method provides the ability to take accurate and reproducible relative data concerning yarn to allow quality review of the yarn based on criteria established by the user.

A second type of event is reported with a triangular icon when there is a crossing of the 1,000 pixel threshold. In this instance the scan filter is chosen as 0 above and 0 below the line so that any reading of at least 1,000 pixels is reported. In an air textured yarn, this then reports a very large loop. Finally, the arrows on page two of FIG. 8 indicate the third threshold and filter setup which is displayed at the top of the output with a fixed threshold (FT) of 325 scans and a filter scan (FS) of 20/2, or 20 scans above the line and two scans below the line. Accordingly, this filtered threshold will report an event consisting of a relatively long balloon followed by a relatively short entanglement, as found at about 170 and 270 centimeters. This figure also shows that the operator has chosen a skip or SKP of four scans. Four skips were used to expand the total length of yarn under study to 2,000 centimeters from the 500 centimeters which would have been stored if every scan had been recorded at the 100 m/min. speed used.

FIG. 9 is an output with a single fixed threshold having a deadband around it with the application of a length filter. The fixed threshold is indicated by the middle line 201 surrounded by upper line 202 and lower line 203 that establish a deadband. This deadband setting effectively establishes two thresholds, one at upper line 202 and one at lower line 203 by the selection of one threshold at line 201 and the size of a band around the threshold. With the deadband, an event is counted after arming above line 202 and then only when the widths go below line 203 again. With this deadband, the yarn diameter will be determined to decrease from above the threshold to below the threshold only if the yarn diameter moves from above the top line 202 to below lower line 203. To this in this case is added a length filter (EL) of three millimeters, meaning that after each event is recorded as indicated by the arrow icons at the bottom of the output the system will ignore scans in the following three millimeters. An event in this instance is a crossing from above to below the deadband. Thus, the system will not detect any new event for a length of three millimeters following a previous event.

The features of the system and method of this invention are further described in the instruction manual for the Profile Tester offered for sale by Lawson-Hemphill, Inc., Central Falls, R.I., incorporated herein by reference.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A yarn profile analyzer, comprising:
an imaging area including a light source and a spaced light sensing array with a plurality of linearly-arranged light-sensing elements each having an output signal;
means for moving yarn through said imaging area between said light source and said sensing array;
means for establishing an array element received light level necessary to indicate that the element has been blocked by the yarn; and
means for determining, from the element output signals, the widths of closely-spaced portions of the yarn passed through the imaging area; said means for determining including means for indicating the furthest-spaced pair of elements blocked by the yarn.

2. The yarn profile analyzer of claim 1 further including means for spreading the yarn as it passes through the imaging area.

3. The yarn profile analyzer of claim 2 in which said means for spreading includes means for pulling the yarn over a hard surface before it enters the imaging area.

4. The yarn profile analyzer of claim 1 in which said means for applying a substantially constant tension includes means for varying the amount of tension applied to the yarn.

5. The yarn profile analyzer of claim 1 in which said means for applying a substantially constant tension includes a biased pivoting arm over which the yarn travels.

6. The yarn profile analyzer of claim 1 in which said means for moving yarn includes means for varying the yarn speed through the imaging area.

7. The yarn profile analyzer of claim 1 in which said means for moving yarn includes a pair of driven rollers downstream of said imaging area.

8. The yarn profile analyzer of claim 1 further including a magnifying lens arrangements in front of said sensing array for increasing the array resolution.

9. The yarn profile analyzer of claim 1 further including means for varying the light output of said light source.

10. The yarn profile analyzer of claim 1 further including means for storing the determined widths.

11. The yarn profile analyzer of claim 1 further including means for establishing a yarn width threshold.

12. The yarn profile analyzer of claim 11 further including means for counting the number of yarn widths greater than or less than said threshold.

13. The yarn profile analyzer of claim 11 further including means for establishing a deadband above and below the threshold for defining a widened yarn width threshold.

14. The yarn profile analyzer of claim 1 further including means for resolving from the determined widths when a local maximum or minimum width has been reached.

15. The yarn profile analyzer of claim 11 further including means for establishing a minimum number of consecutive determined widths which must be greater than or less than said threshold.

16. The yarn profile analyzer of claim 1 further including means for reporting determined widths, including means for reporting only selected ones of the determined widths.

17. The yarn profile analyzer of claim 16 in which said means for reporting only selected ones of the determined widths includes means for not reporting a constant number of determined widths between each reported width.

18. A method of measuring yarn profiles, comprising:
moving the yarn at a constant velocity;
imaging the moving yarn including directing light at the moving yarn and collecting light after passing by the yarn with a linear light sensing array having a plurality of elements;

establishing an array element received light level necessary to indicate that the element has been blocked by the yarn; and determining from the image the widths of closely-spaced portions of the yarn including indicating the furthest-spaced pair of array elements blocked by the yarn.

19. The yarn measuring method of claim 18 further including magnifying the yarn image.

20. The yarn measuring method of claim 18 further including varying the amount of light directed at the moving yarn.

21. The yarn measuring method of claim 18 further including storing the widths.

22. The yarn measuring method of claim 18 further including establishing a yarn width threshold.

23. The yarn measuring method of claim 22 further including counting the number of yarn widths greater or less than the threshold.

24. The yarn measuring method of claim 22 further including establishing a width zone above and below the threshold.

25. The yarn measuring method of claim 22 further including establishing a minimum number of consecutive widths which must be greater than or less than the threshold.

26. The yarn measuring method of claim 18 further including resolving from the widths when a local maximum or minimum width has been reached.

27. The yarn measuring method of claim 18 further including spreading the yarn before it is imaged.

28. The yarn measuring method of claim 18 further including ignoring a predetermined number of widths.

29. The yarn profile analyzer of claim 1 further including means for applying a substantially constant tension to the yarn in said imaging area.

30. The yarn measuring method of claim 18 in which moving the yarn includes moving the yarn at a constant tension.

* * * * *